United States Patent
Franz

(10) Patent No.: US 7,303,761 B2
(45) Date of Patent: Dec. 4, 2007

(54) STABILISED PHARMACEUTICAL COMPOSITION COMPRISING AN EXTENDED RELEASE NON-STEROIDAL ANTI-INFLAMMATORY AGENT AND AN IMMEDIATE RELEASE PROSTAGLANDIN

(75) Inventor: Michel Franz, Brussels (BE)

(73) Assignee: SPRL FRANPharma, Brussels (BE)

( * ) Notice: Subject to any disclaimer, the term of this patent is extended or adjusted under 35 U.S.C. 154(b) by 94 days.

(21) Appl. No.: 10/789,174

(22) Filed: Feb. 26, 2004

(65) Prior Publication Data

US 2004/0185100 A1  Sep. 23, 2004

Related U.S. Application Data

(60) Provisional application No. 60/451,827, filed on Mar. 3, 2003.

(30) Foreign Application Priority Data

Jan. 9, 2004  (EP)  .................. 04447005

(51) Int. Cl.
*A61K 9/52*  (2006.01)

(52) U.S. Cl. ...................... 424/457; 424/451

(58) Field of Classification Search ...................... None
See application file for complete search history.

(56) References Cited

U.S. PATENT DOCUMENTS

| 5,213,807 | A | * | 5/1993 | Chemburkar et al. ....... 424/472 |
| 5,601,843 | A | | 2/1997 | Gimet et al. |
| 6,183,779 | B1 | * | 2/2001 | Ouali et al. .................. 424/472 |
| 6,193,779 | B1 | | 2/2001 | Reichert et al. |
| 6,312,724 | B1 | | 11/2001 | Odidi et al. |
| 6,365,184 | B1 | | 4/2002 | Depui et al. |
| 6,537,582 | B2 | | 3/2003 | Woolfe et al. |
| 6,544,556 | B1 | | 4/2003 | Chen et al. |
| 6,613,354 | B2 | | 9/2003 | Depui et al. |
| 6,656,503 | B1 | * | 12/2003 | Sherman ...................... 424/474 |
| 2002/0054908 | A1 | | 5/2002 | Woolfe et al. |
| 2003/0138486 | A1 | * | 7/2003 | Ouadji ........................ 424/466 |

FOREIGN PATENT DOCUMENTS

| WO | 99/65496 | 12/1999 |
| WO | 02/22108 | 3/2002 |

OTHER PUBLICATIONS

United States Pharmacopeia, Official Monographs p. 554 & 556 (2003).
Quality of Prolonged Release Oral Solid Dosage Forms p. 167-174. (1992).
Rowe et al. Handbook of Pharmaceutical Excipients, Fourth Edition, Polymethacrylates p. 462-465, Hypromellose Phthalate p. 301-305, Hypromellose p. 297-300. (2003).
Diclofenac Sodium Extended-Release Tablets, The United States Pharmacopeial Forum vol. 47(1) Jan.-Feb. 2003 p. 319-320.
Diclofenac Sodium Extended-Release Tablets, Pharmacopeial Forum vol. 30(2), Mar.-Apr. 2004 p. 476-478.
Novatis Pharmaceuticals—Voltaren. http://pharma.us.novartis.com/products/name/voltarenxr.jsp Mar. 27, 2005. Copyright 2005.

\* cited by examiner

*Primary Examiner*—Michael P. Woodward
*Assistant Examiner*—Eric E. Silverman
(74) *Attorney, Agent, or Firm*—Merchant & Gould P.C.

(57) ABSTRACT

The present invention is related to a solid pharmaceutical composition comprising two separate regions,
- a first region comprising at least one non-steroidal anti-inflammatory drug (NSAID) and an adequate pharmaceutical carrier containing a retardant material for an extended release delivery of said non-steroidal anti-inflammatory drug (NSAID), and
- a second region comprising a stabilized gastroprotective prostaglandin and an adequate pharmaceutical carrier for an immediate release of said stabilized gastroprotective prostaglandin.

18 Claims, No Drawings

STABILISED PHARMACEUTICAL COMPOSITION COMPRISING AN EXTENDED RELEASE NON-STEROIDAL ANTI-INFLAMMATORY AGENT AND AN IMMEDIATE RELEASE PROSTAGLANDIN

This application claims benefit to provisional application Ser. No. 60/451,827, filed Mar. 3, 2003, entitled "STABILISED PHARMACEUTICAL COMPOSITION COMPRISING AN EXTENDED RELEASE NON-STEROIDAL ANTI-INFLAMMATORY AGENT AND AN IMMEDIATE RELEASE PROSTAGLANDIN", which is specifically incorporated by reference herein.

FIELD OF THE INVENTION

The present invention is related to a pharmaceutical composition based upon a dual release dosage form comprising an adequate pharmaceutical carrier, an extended release non-steroidal anti-inflammatory drug (NSAID) and an immediate release stabilized prostaglandin. The present invention is also related to the use of said pharmaceutical composition for the treatment of inflammatory conditions or diseases, like osteoarthritis and rheumatoid arthritis.

BACKGROUND OF THE INVENTION AND STATE OF THE ART

Non-steroidal anti-inflammatory drugs (NSAIDs) have demonstrated high therapeutic value, especially for the treatment of inflammatory conditions or diseases, like osteoarthritis and rheumatoid arthritis.

A great variety of NSAIDs dosage forms is available on the market.

Usually, the NSAIDs have to be taken several times a day, which can generate an important compliance issue, particularly with patients population like the elderly.

As understood in the prior art, enteric or delay release coatings are not an efficient method for the delivery of NSAIDs due to the inability of such formulations to provide or achieve a sustained therapeutic effect due to the lack of prolonged release of the pharmaceutical agent. Also the concurrent administration of enteric coated or delayed release NSAIDs with food or the presence of food in the stomach may lead to dose dumping and unwanted secondary effects.

Optimizing the release of one or several drugs from a dosage form is an important way of guiding their pharmacological action and of great benefit for patient treatment. Extended release (identified by the abbreviations ER or XR) is the most current and official terminology to define a controlled availability of the drug alongside the gastrointestinal tract. Other expressions used in the scientific literature to define the same profile are: sustained, controlled, prolonged, retard or similar.

Modified releases have been debated between Experts in the Pharmaceutical Technology and are frequently defined in scientific and official documents.

In the NSAIDS therapeutic class, the United States Pharmacopeia, 25 edition, pages 554-555, describes the Diclofenac Sodium Delayed-Release Tablets in an Official Monograph.

Interestingly, a proposal of a Diclofenac Sodium Extended-Release Tablets monograph has been recently published on the USP Pharmacopeial Forum (Vol. 2003 pp. 319-320).

More details on Diclofenac Sodium, i.e., about Pharmacokinetics data, can be found in the Prescribing Information document made by Novartis, the Company which commercialised the drug initially.

The NSAIDS exert most of their anti-inflammatory, analgesic and antipyretic activity and inhibit hormone-induced uterine contractions and certain types of cancer growth trough inhibition of prostaglandin G/H synthase, also known as cyclooxygenase (COX). Inhibition of COX-1 causes a number of side effects including inhibition of platelet aggregation associated with disorders of coagulation, and gastrointestinal side effects. The gastrointestinal side effects are due to a decrease in the biosynthesis of prostaglandins which are cytoprotective of the gastric mucosa. The prevalence of gastrointestinal side effects is similar among "acute" and "chronic" NSAID users and affects especially the elderly.

A high incidence of side effects has historically been associated with the use of classic cyclooxygenase inhibitors, all of which are about equipotent for COX-1 or COX-2, or which are COX-1.

In view of the still very large therapeutic use of classic NSAIDs, several approaches have been undertaken to minimise the drugs' adverse effects.

For many years, neutralization of gastric acid with antiacids was the only relief from the gastrointestinal pain induced by ulcers. More recently agents called "proton pomp inhibitors" have been recommended and used. They provide a more specific class of inhibitors of gastric secretion in mammals, including humans, by blocking the final step of acid production.

The documents U.S. Pat. No. 6,365,184, U.S. Pat. No. 6,544,556 and U.S. Pat. No. 6,613,354 describe an oral pharmaceutical dosage form comprising a "proton pomp inhibitor" and one or more NSAID(s) in a fixed formulation, and their use in the treatment of gastrointestinal side-effects associated with NSAID treatment.

The use of prostaglandins is an improved way to minimize the gastrointestinal ulcerations induced by the oral administration of NSAIDs, such PGE1, PGE2, misoprostol and derivatives thereof.

Co-administering exogenous prostaglandins, particularly misoprostol, in association with NSAIDS is a "natural" way of preventing NSAID-associated ulcers and ulcer complications as described in Silverstein F. E., Digestive Diseases and Sciences 1998; 43: 447-458.

Moreover, dosage forms based on misoprostol or anti-ulcerogenic prostaglandins are cheaper than the commercially available "proton pump inhibitors". This results in "fixed dose combination products" priced lower, which is an important parameter in the today Social Security resources.

More details on Misoprostol, i.e., about Pharmacokinetics document data, can be found in the Prescribing Information document made by Searle, the Company which commercialised the drug initially.

Interestingly, the European Pharmacopeia Commission has, in June 2003, proposed a monograph for the Misoprostol active ingredient. The document is Monograph No.: 1731 with additional reference PA/PH/Exp.10B/T (02)140 ANP and is currently submitted for comment to the relevant authorities.

However, prostaglandins are unstable compounds and have been shown degrading readily in the presence of NSAIDs.

The documents U.S. Pat. No. 5,601,843, U.S. Pat. No. 6,193,779, U.S. Pat. No. 6,537,582 and WO99/65496 describe different ways of combining sodium diclofenac Enteric- or Delayed-Coated Releases with a prostaglandin.

However, these approaches have the drawbacks of the enteric or delay releases dosage forms highlighted here above.

Therefore, there is a need in the art to provide a composition for administering an NSAID sustained release dosage form wherein the undesirable gastrointestinal side effects of the drug are minimised.

AIMS OF THE INVENTION

The present invention aims to provide a pharmaceutical composition which does not present the drawbacks of the state of the art and which finds an adequate solution for the above-mentioned problem.

A particular aim of the present invention is to provide such a composition that allows an extended release delivery of non-steroidal anti-inflammatory agents and allows an immediate release of the prostaglandin.

SUMMARY OF THE INVENTION

The present invention is related to a solid pharmaceutical composition comprising at least two separate regions (or portions), wherein a first region (or portion) comprises at least one non-steroidal anti-inflammatory drug (NSAID) associated with an adequate pharmaceutical carrier containing a retardant material for said non-steroidal anti-inflammatory drug (NSAID), and a second region (or portion) comprises a prostaglandin, preferably a stabilized prostaglandin, and an adequate pharmaceutical carrier with an immediate release.

According to the invention, "a solid pharmaceutical composition" means a dosage form which is adequate for oral administration.

In said composition, the retardant material and the immediate release carrier are two elements selected in order to allow respectively an extended (or sustained) release delivery of the non-steroidal anti-inflammatory agent and to provide the prostaglandin immediately available for absorption.

Furthermore, the composition comprises an element such as an adequate pharmaceutical carrier which allows a stabilization of the prostaglandin.

Advantageously, the pharmaceutical composition according to the invention comprises a first and a second regions that are separated by a third region, which is a protective intermediate region that does not comprise any therapeutically active compound.

The first region of the pharmaceutical composition of the invention comprises extended release formulations of the NSAID which eliminate the issue of compliance as designed to be dosed once or twice a day, providing therapeutically effective plasma levels over a long period of time.

Pharmaceutical technology uses several approaches to design dosage forms with an extended release delivery.

The retardant material included in the first region is in dosage forms to create an extended delivery of the NSAID compound(s) for at least up to 24 hours in human patients and can include one or more pharmaceutically acceptable hydrophilic materials and/or hydrophobic materials which are capable of imparting controlled release of the active agent in accordance with the present invention.

The said retardant material is preferably selected from the group consisting of acrylic and methacrylic acid polymers and copolymers, alkylcelluloses, gums, protein derived materials or a mixture thereof. Are also suitable lipidic materials like waxes, glycerides or aliphatic alcohols. Ther retardant materials can be used alone or in mixture.

In a preferred embodiment of the present invention, the above-mentioned hydrophobic material of the first region is an acrylic polymer selected from the group consisting of acrylic acid and methacrylic acid copolymers, methylacrylate polymers, methyl methylacrylate copolymers, ethoxyethyl methacrylate polymers, cyanoethylmethacrylate polymers, aminoalkyl methacrylate copolymers, poly(acetylic acid), poly(methacrylic acid), methacrylic acid alkylamine copolymers, poly(methyl methacrylate) polymers, poly(methacrylic acid) (anhydride), polymethacrylate polymers, polyacrylamide, poly(methacrylic acid anhydride), glycidyl methacrylate copolymers or a mixture thereof.

According to another preferred embodiment of the present invention, the said retardant material is an alkylcellulose selected from the group consisting of hydroxypropylmethylcelluloses (HPMC), hydroxyethylcelluloses (HEC), hydroxypropylethylcelluloses (HPEC), hydroxypropylcelluloses (HPC), methylcelluloses (MC), ethylcelluloses (EC) or sodium carboxymethylcelluloses (NaCMC) (possibly said celluloses modified by addition of functional groups) or a mixture thereof.

Preferred examples of suitable retardant materials included in the pharmaceutical composition of the invention are lipidic materials, methacrylic acid copolymers or cellulose-based polymers.

It is to be noted that said listing is not meant to be exclusive, and that any pharmaceutically acceptable hydrophobic material and/or hydrophilic material which is capable of imparting extended release of the active agent(s) may be used in accordance with the present invention.

The percentage of these retardant molecules in the pharmaceutical composition according to the invention can also be adapted by the person skilled in the art according to the amount and/or the type of the active agents present in said composition.

Furthermore, organic or inorganic ingredients can be introduced in the different regions (or portions) of the composition to modulate the release of the NSAID(s) from the first region (or portion). For example, a phosphate buffer can be introduced to create a pH of about 4.5 or a suitable quantity of an organic acid to create lower pH conditions.

In addition to the above ingredients, suitable quantities of other elements, e.g. diluents, lubricants, binders, granulating aids, colorants, flavorants and glidants that are conventional in the pharmaceutical art can be present in the first region (the region containing NSAID) of the pharmaceutical composition according to the invention. The quantities of these additional elements will be sufficient to provide the desired effect to the desired (solid) formulation.

The second region (the (preferably stabilized gastroprotective) prostaglandin-containing region) comprises an adequate pharmaceutical carrier for improving the immediate release of said (stabilized gastroprotective) prostaglandin.

Said pharmaceutical carrier is an immediate release formulation that offers a fast disintegration, resulting in a short dissolution period, followed by a quick absorption of the stabilized prostaglandin derivative.

Therefore, following the administration of the pharmaceutical composition according to the invention, the quick appearance of the prostaglandin in the blood is advantageous as it can start to work immediately against the deleterious side effects of the NSAID.

However, the prostaglandins chemical class of compounds is known to include drugs which are very potent, but also very unstable and can degrade rapidly in presence of NSAIDs.

To stabilize advantageously the prostaglandins used as anti-ulcerogenic drugs, it is possible to use (preferably under the form of a dispersion) stabilizing (gastroprotective) agents such as hydroxypropylmethylcellulose (HPMC), or polyvinylpyrrolidone (PVP).

Other stabilizing agents include, but are not limited to: cellulosic polymers such as hydroxypropyl cellulose (HPC), hydroxyethyl cellulose (HEC), methyl cellulose (MC), ethyl cellulose (EC), cellulose acetate, cellulose acetate phthalate, cellulose acetate trimellitate, hydroxypropyl methylcellulose phthalate, microcrystalline cellulose and sodium carboxymethylcellulose (NaCMC); and vinyl polymers and copolymers such as polyvinylacetate phthalate, vinylacetate crotonic acid copolymers, and ethylene-vinyl acetate copolymers or a mixture thereof. The prostaglandin stabilizing agent is present in an amount effective to provide the desired stabilizing effect; generally, this means that the ratio of prostaglandin/stabilizing agent is at least about 1:500 w/w, more preferably about 1:99 w/w.

The prostaglandin-containing second region contains various excipients that do not exhibit a destabilizing effect and include, for example, binders, bulking agents, diluents, disintegrants, lubricants, fillers, carriers, and the like.

In the present invention, the non-steroidal anti-inflammatory agents present in the first region are preferably selected from the group consisting of: aceclofenac, diclofenac, diflunisal, fenbufen, flufenamic acid, ibuprofen, indomethacin, ketoprofen, meclofenamate sodium, meloxicam, mefenamic acid, nabumetone, naproxen, piroxicam, suprofen, tiaprofenic acid, acetylsalicylic acid, flurbiprofen, ketorolac, oxaprozin, sulindac, tenoxicam, tiaprofenic acid and suitable salts, esters, amides, prodrugs or analogues thereof.

The pharmaceutical composition according to the invention could also comprise pharmaceutical acceptable analogues or derivatives of these non-steroidal anti-inflammatory agents.

In the pharmaceutical composition according to the invention, the prostaglandins present in the second region are preferably selected from the group consisting of the "E-series" prostaglandins, such as PGE1, PGE2, misoprostol, enoprostol, enisoprost, rosaprostol or miraprostol and pharmaceutical acceptable analogues or derivatives thereof. The preferred prostaglandins are "anti-ulcerogenic" prostaglandins.

The pharmaceutical composition according to the invention is suitable for the treatment of inflammatory conditions, such as exhibited inflammatory diseases, like osteoarthritis and rheumatoid arthritis.

The present invention is also related to a packaging preferably designed to minimize the oxygen permeation and to contain the pharmaceutical composition according to the invention and one or more gastric antisecretory prostaglandin analogue medicament(s).

The present invention will be described in detail in the following description which is presented as a non-limiting illustration of the various aspects of the present invention.

DETAILED DESCRIPTION OF THE INVENTION

The invention, as noted above, is in one embodiment a stabilised pharmaceutical composition for administration of an NSAID and a prostaglandin, wherein the NSAID is in a form that allows an extended release and the prostaglandin is in a form which allows an immediate release. The solid composition is comprised of at least two discrete regions (or portions).

The regions can contain different active or inactive ingredients, can have different roles in the composition, can influence the release of the active ingredients, can facilitate the separation of the active ingredients to improve compatibility and stability and can be made of a single or of multiple units comprising (or not) the active compounds.

Preferably, the composition comprises a first region (or portion) wherein the extended release NSAID is present and a second region (or portion) wherein the immediate release prostaglandin is present.

A further region (or portion) can serve to separate the different layers or regions comprising the active ingredients or to facilitate the design of the dosage form.

Furthermore, dosage forms with two discrete regions (or portions) are suitable to design very different release characteristics for the active ingredients contained in the different regions (or portions), allowing the dual release of the pharmaceutical composition of the invention. Secondarily, they offer the possibility of imparting a repeat-action effect of one or each of the two active ingredients.

The invention is not limited with respect to the selected mentioned NSAID; the dual and stabilised compositions of the invention can contain any NSAID, NSAID derivative, or combination of NSAIDs. Typical NSAIDs include, but are not limited to, aceclofenac, acetylsalicylic acid, diclofenac, diflunisal, fenbufen, flufenamic acid, flurbiprofen, ibuprofen, indomethacin, ketorolac, meloxicam, mefenamic acid, naproxen, oxaprozin, piroxicam, sulindac, tenoxicam, diflunisal and tiaprofenic acid. Pharmaceutically acceptable analogues of such NSAIDs are suitable as well; particularly analogues of aceclofenac, diclofenac, ketoprofen, piroxicam, meloxicam, naproxen, tenoxicam and their salts are preferred.

The NSAID is present in the composition in a therapeutically effective amount; preferably, the solid composition is unit dosage form. The amount of NSAID administered will depend on the age, weight, and general condition of the subject, the severity of the condition being treated, and the judgement of the prescribing physician. Suitable therapeutic amounts will be known to those skilled in the art and/or are described in the pertinent reference texts and literature. For aceclofenac a therapeutic dose is typically about 50 mg to about 200 mg per dosage form. For diclofenac, acid or sodium or potassium salts for example, a therapeutic dose is typically about 50 to about 150 mg per dosage form, optimally about 75 mg or about 100 mg per dosage form. For ketoprofen, the therapeutic dose is typically 100 mg to 300 mg. The therapeutic dosing range for a dosage containing meloxicam, piroxicam or tenoxicam is about 5 mg to about 40 mg per dosage form, optimally about 10 mg or about 20 mg per dosage form, while the therapeutic dosing range for a tablet containing naproxen is about 250 mg to about 1000 mg per dosage form.

The NSAID-containing region (or portion) can also contain various excipients, as is well known in the pharmaceutical art, provided such excipients do not exhibit a destabilising effect on any components in the dual release dosage form composition.

The second region (or portion) in the dual-release dosage form contains a prostaglandin to reduce or eliminate the undesirable side effects of the NSAID following oral administration. Preferred prostaglandins are those, which are effective in this regard, i.e. are typically "anti-ulcerogenic".

The prostaglandin is preferably selected from the "E-series" prostaglandins such PGE1, PGE2, misoprostol, enoprostol, enisoprost, rosaprostol or miraprostol and pharmaceutical acceptable analogues or derivatives thereof. The most preferred prostaglandin is misoprostol, present in an amount of about 50 to about 500 micrograms per dosage form, more preferably about 100 to about 300 micrograms per dosage form. Misoprostol leaves rapidly the immediate release region, is rapidly absorbed and produces quickly its antisecretory effect, reducing or eliminating the ulcerogenicity of the NSAID.

A cellulose-based polymer, preferably Hypromellose, also called HPMC, is used to stabilise the prostaglandin. The stabilising agent is present in an amount effective to provide the desired stabilising effect; generally, this means that the ratio of prostaglandin to the prostaglandin stabilising agent is at least about 1:500 w/w, more preferably about 1:99 w/w.

The active ingredients in the present composition, i.e., both the NSAID and the prostaglandin, may be administered in the form of a pharmacologically acceptable acid, salt, ester, amide, prodrug or analogue or as a combination thereof.

A third region can be present in the dual release dosage form depending on its design or the need to better separate the different active ingredients. If existing, the third region will contain no NSAID or prostaglandin but various excipients that do not exhibit a destabilising effect on any components in the dual release dosage form.

Coating can be present in one or several regions of the invention. It can be used as a part of the first region (or portion) to act as a retardant material in the release of the NSAID. It can also be used to facilitate the segregation (physical and chemical separation) between the active ingredients. A number of coating agents are commercially available and pharmaceutically acceptable, in particular methacrylic and/or acrylic acid copolymers or cellulose based polymers.

Details on suitable coating agents are well known by the person skilled in the pharmaceutical art.

The dosage form of the pharmaceutical composition according to the invention can be formulated as any suitable tablet, core tablet, layered or multi-layered tablet, or multiple unit tablets or as any suitable capsule, or a combination of said formulations obtained by known machines able to produce the dosage forms of the invention in conditions imposed by the pharmaceutical laws.

DESCRIPTION OF PREFERRED EMBODIMENTS OF THE INVENTION

Core Tablet

The core is the first region (or portion) containing the NSAID when a core tablet is designed as a dosage form of the invention. A coating may surround the core to prevent direct contact between the NSAID and the prostaglandin and to avoid non-beneficial interaction such as degradation of the prostaglandin. The dimensions of the core are suitable to allow mantle dry coating with the immediate release prostaglandin containing second region while finishing with a palatable dosage form.

Upon ingestion, the mantle disintegrates quickly, which liberates the two regions of the dosage form and allows the dual release.

A retardant material, in particular selected among the group consisting of lipidic materials, methacrylic and/or acrylic acid copolymers or cellulose based polymers, is used to create the extended release of the NSAID in the first region.

The second region will be designed as a mantle made by direct compression to minimize the degradation of the prostaglandin and to provide fast disintegration and dissolution.

Details on other suitable materials and their quantities are well known by them skilled in the pharmaceutical art as are the available technologies to manufacture and control the core tablets.

Layered or Multi-layered Tablets

In layered tablets, the NSAID drug and the suitable excipients may be compressed in the lower half of the tablet to become the first region (or portion) of the dosage form. The prostaglandin together with the suitable excipients can be superposed and pressed onto it and be the second region (or portion) of the dosage form. A third region (or portion) containing no drug can provide a barrier between the two active ingredient containing layers and prevent any non-beneficial interaction such a degradation of the prostaglandin.

Upon ingestion, the layers separate quickly, which liberates the regions (or portions) of the dosage form and allows the dual release.

The retardant material(s) used to create the extended release of the NSAID in the first region (or portion) can be selected from the group described in the summary, in particular lipidic materials, methacrylic and/or acrylic acid copolymers or cellulose based polymers.

The second region (or portion) will be designed as a layer made by direct compression to minimize the degradation of the prostaglandin and to provide fast disintegration and dissolution.

When present the third region (or portion) is made of inert excipients suitable for direct compression and separates the 2 other regions.

Details on other suitable materials and their quantities are well known by them skilled in the pharmaceutical art as are the available technologies to manufacture and control the core tablets.

Multiple Unit Tablets

The first region (or portion) can be made of granulates, beads, pellets, mini-tablets or similar units or a mixture of them, formulated to allow the sustained delivery of the NSAID. The multiple units can be coated with a retardant material or to prevent direct contact between the 2 regions. The multiple units should be soft enough to deform only slightly under compression to avoid agglomeration with the second region (or portion) and modification of the release of one or of the two active ingredients.

A retardant material, in particular selected among the group consisting of lipidic materials, methacrylic and/or acrylic acid copolymers or cellulose based polymers, is used to create the extended release of the NSAID in the first region (or portion).

The second region (or portion) can be made of one or several units or of a powder, both directly compressible, to minimize the degradation of the prostaglandin and to provide fast disintegration and dissolution.

Details on other suitable materials and their quantities are well known by them skilled in the pharmaceutical art as are available technologies to manufacture and control the multiple unit tablets.

Capsules

Hard gelatine capsules (capsules) can also be very useful to design suitable dosage forms for dual release as they may contain multiple units corresponding to the different regions (or portions).

Capsules are made from different polymers as gelatine or starch for example. Interestingly, capsules made of the cellulose derivative hydroxypropylmethylcellulose (HPMC) are particularly advantageous for the present invention. They are more suited than the gelatine based capsules for example because they offer the advantage of a low humidity content. The classical hard gelatine capsules are using moisture as a plasticizer and their high water content has been proven harmful for sensitive drugs like the prostaglandins. Interestingly, the water content of the HPMC hard gelatine capsules is limited to maximum 6% and it can even been lowered by drying before use.

The first region (or portion) of the HPMC capsule is made of granulates, beads, pellets or mini-tablets or similar multiple units or of a mixture of them and contains the NSAID drug formulated with an extended release.

A retardant material, in particular selected among the group consisting of lipidic materials, methacrylic and/or acrylic acid copolymers or cellulose based polymers, is used to create the extended release of the NSAID in the first region (or portion).

The second region (or portion) of the HPMC capsule will be made of a powder or of one or several units.

Units of the first and/or second region (or portion) can be coated to prevent direct contact between the NSAID and the prostaglandin and to avoid non-beneficial interaction such as degradation of the prostaglandin.

Upon ingestion, the HPMC capsule dissolves, which liberates the two regions (or portions) of the dosage form and allows the dual release.

Details on other suitable materials and their quantities are well known by them skilled in the pharmaceutical art as are available technologies to manufacture and control capsules containing multiple units.

EXAMPLES

The examples are described for the purposes of illustration and are not intended to limit the scope of the invention.

Methods referred to but not explicitly described in this disclosure and examples are reported in the literature and are well known to those skilled in the art.

Example 1

Region 1 for Layered Tablets

Different grades and concentrations of hypromellose have been tested in the design of the first region of layered tablets. Tablets of 9 mm diameter and weighing 225 mg have been chosen.

The influence on the diclofenac sodium extended release of the concentration and grades of the Hypromellose 4000 mPa.s was noted, as was the use of dibasic calcium phosphate. The influence of the addition of 10% Hypromellose 100, 10% lactose or of 10% Dibasic Calcium phosphate was also noted.

| 30% Hypromellose 4000 | |
|---|---|
| Diclofenac sodium | 75.0 mg |
| Hypromellose 4000 mPa · s | 70.0 mg |
| Microcristalline cellulose | 30.0 mg |
| Lactose | 44.6 mg |
| Colloidal silicon dioxide | 0.4 mg |
| Magnesium stearate | 5.0 mg |

| 40% Hypromellose 4000 | |
|---|---|
| Diclofenac sodium | 75.0 mg |
| Hypromellose 4000 mPa · s | 90.0 mg |
| Lactose | 54.6 mg |
| Colloidal silicon dioxide | 0.4 mg |
| Magnesium stearate | 5.0 mg |

| 30% Hypromellose 4000 + 10% Hypromellose 100 | |
|---|---|
| Diclofenac sodium | 75.0 mg |
| Hypromellose 4000 mPa · s | 70.0 mg |
| Hypromellose 100 mPa · s | 20.0 mg |
| Lactose | 54.6 mg |
| Colloidal silicon dioxide | 0.4 mg |
| Magnesium Stearate | 5.0 mg |

| 50% Hypromellose 4000 | |
|---|---|
| Diclofenac sodium | 75.0 mg |
| Hypromellose 4000 mPa · s | 115.0 mg |
| Microcristalline cellulose | 29.6 mg |
| Colloidal silicon dioxide | 0.4 mg |
| Magnesium Stearate | 5.0 mg |

| 30% Hypromellose 4000: Dibasic calcium phosphate | |
|---|---|
| Diclofenac sodium | 75.0 mg |
| Hypromellose 4000 mPa · s | 70.0 mg |
| Dibasic calcium phosphate | 74.6 mg |
| Colloidal silicon dioxide | 0.4 mg |
| Magnesium Stearate | 5.0 mg |

Example 2

Bi-layered Tablets

Tablets dosed at 75 mg of diclofenac sodium and 200 μg misoprostol (9 mm diameter, total weight: 325 mg) have been prepared using this formulation.

Diclofenac sodium extended release was shown and compared to a marketed product.

Misoprostol immediate release is not shown but is similar to the one obtained with a commercially available product.

| Diclofenac sodium ER region (225 mg) | |
|---|---|
| Diclofenac sodium | 75.0 mg |
| Hypromellose 4000 mPa · s | 70.0 mg |
| Hypromellose 100 mPa · s | 20.0 mg |
| Lactose | 34.6 mg |
| Dibasic calcium phosphate | 20.0 mg |
| Colloidal silicon dioxide | 0.4 mg |
| Magnesium stearate | 5.0 mg |

| Stabilized Misoprostol IR region (100 mg) | |
|---|---|
| Misoprostol 1% dispersion HPMC | 20.0 mg |
| Microcristalline cellulose | 25.0 mg |
| Lactose | 48.8 mg |
| Crospovidone | 5.0 mg |
| Colloidal silicon dioxide | 0.2 mg |
| Glycerol behenate | 1.0 mg |

Example 3

Bi-layered Tablets

A formulation of the first region of tablets dosed at 100 mg of diclofenac sodium is described. The second region is dosed at 200 µg of misoprostol and is the same than the one in example 2. The bi-layered tablet is of 9 mm diameter and weights 330 mg.

| Diclofenac sodium ER region (230 mg) | |
|---|---|
| Diclofenac sodium | 100.0 mg |
| Hypromellose 4000 mPa · s | 70.0 mg |
| Hypromellose 100 mPa · s | 20.0 mg |
| Lactose | 24.6 mg |
| Dibasic calcium phosphate | 10.0 mg |
| Colloidal silicon dioxide | 0.4 mg |
| Magnesium stearate | 5.0 mg |

Example 4

Tri-layered Tablets

Tablets dosed at 75 mg of diclofenac sodium and 200 µg of misoprostol (9 mm diameter, total weight: 425 mg) are defined.

The first and the second region are the same than the ones described in example 2.

A third intermediate region is used in this formulation. Details on the composition of the third region are provided.

| Protective intermediate region (100 mg) | |
|---|---|
| Hypromellose 5 mPa · s | 20.0 mg |
| Microcristalline cellulose | 25.0 mg |
| Lactose | 48.8 mg |
| Crospovidone | 5.0 mg |
| Colloidal silicon dioxide | 0.2 mg |
| Glycerol behenate | 1.0 mg |

Example 5

Tri-layered Tablets

Tablets dosed at 100 mg of diclofenac sodium and 200 µg of misoprostol (9 mm diameter, total weight: 428 mg) are defined.

The formulation of the first region dosed at 100 mg of diclofenac sodium is described.

The second region dosed at 200 µg of misoprostol is the same than the one described in example 2 and the third region is formulated as in example 4.

| Diclofenac sodium ER region (228 mg) | |
|---|---|
| Diclofenac sodium | 100.0 mg |
| Hydroxyethylcellulose | 80.0 mg |
| Lactose | 30.0 mg |
| Colloidal silicon dioxide | 1.0 mg |
| Povidone | 9.0 mg |
| Talc | 3.0 mg |
| Magnesium stearate | 5.0 mg |

Example 6

Core Tablets

Tablets dosed at 75 mg of diclofenac sodium and 200 µg misoprostol (11 mm diameter biconvex, total weight: 495 mg) have been prepared using this formulation.

Diclofenac sodium extended release from the first region is shown and compared to a marketed product in FIG. 2. A protective coating is part of the first region.

Misoprostol immediate release from the second region is not shown but is similar to the one obtained with a commercially available product.

| Diclofenac sodium ER region (150 mg) | |
|---|---|
| Diclofenac sodium | 75.0 mg |
| Hypromellose 4000 mPa · s | 50.0 mg |
| Hypromellose 100 mPa · s | 10.0 mg |
| Lactose | 11.8 mg |
| Colloidal silicon dioxide | 0.2 mg |
| Magnesium stearate | 3.0 mg |

| Protective coating (5 mg) | |
|---|---|
| Hypromellose 5 mPa · s | 4.5 mg |
| Macrogol 6000 | 0.5 mg |
| Purified water* | |

*Removed during the process

| Stabilized Misoprostol IR region (340 mg) | |
|---|---|
| Misoprostol: HPMC 1% dispersion | 20.0 mg |
| Microcristalline cellulose | 299.5 mg |
| Crospovidone | 15.0 mg |

-continued

| Stabilized Misoprostol IR region (340 mg) | |
|---|---|
| Colloidal silicon dioxide | 0.5 mg |
| Glycerol behenate | 5.0 mg |

Example 7

Core Tablets

Tablets dosed at 100 mg of diclofenac sodium and 200 µg misoprostol (11 mm diameter biconvex, total weight: 505 mg) are defined.

| Diclofenac sodium ER region (160 mg) | |
|---|---|
| Diclofenac sodium | 100.0 mg |
| Hypromellose 4000 mPa · s | 45.0 mg |
| Hypromellose 100 mPa · s | 10.0 mg |
| Dibasic calcium phosphate | 1.8 mg |
| Colloidal silicon dioxide | 0.2 mg |
| Magnesium stearate | 3.0 mg |

| Protective core coating (5 mg) | |
|---|---|
| Hypromellose 5 mPa · s | 4.5 mg |
| Macrogol 6000 | 0.5 mg |
| Purified water* | |

*Removed during the process

| Stabilized Misoprostol IR region (340 mg) | |
|---|---|
| Misoprostol: HPMC 1% dispersion | 20.0 mg |
| Microcristalline cellulose | 299.5 mg |
| Crospovidone | 15.0 mg |
| Colloidal silicon dioxide | 0.5 mg |
| Glycerol behenate | 5.0 mg |

Example 8

HPMC Capsules Containing Mini-tablets

HPMC based, 0 size HPMC capsules dosed at 75 mg of diclofenac sodium and 200 µg misoprostol have been prepared.

The region 1 is made of 6 extended release film coated mini-tablets (4 mm diameter, 41 mg) and the region 2 of one immediate release mini-tablet (4 mm diameter, 45 mg).

The 2 regions are prepared separately and introduced in the empty HPMC capsules using a suitable capsule filling machine.

Diclofenac sodium extended release was shown and compared to a marketed product in.

Misoprostol immediate release is not shown but is similar to the one obtained with commercially available products.

The total net weight of the HPMC capsule is 291 mg.

| Diclofenac sodium ER mini-tablets (40 mg) | |
|---|---|
| Diclofenac sodium | 12.5 mg |
| Ethylcellulose 10 | 20.0 mg |
| Monobasic sodium phosphate | 6.7 mg |
| Colloidal silicon dioxide | 0.05 mg |
| Magnesium stearate | 0.75 mg |

| Protective core coating (1 mg) | |
|---|---|
| Hypromellose 5 mPa · s | 0.9 mg |
| Macrogol 6000 | 0.1 mg |
| Purified water* | |

*Removed during the process

| Misoprostol IR mini-tablet (45 mg) | |
|---|---|
| Misoprostol: HPMC 1% dispersion | 20.0 mg |
| Microcristalline cellulose | 13.0 mg |
| Lactose | 9.4 mg |
| Crospovidone | 2.0 mg |
| Colloidal silicon dioxide | 0.1 mg |
| Hydrogenated castor oil | 0.5 mg |

Example 9

HPMC Capsules Containing Mini-tablets

HPMC based, elongated 0 size capsules dosed at 100 mg of diclofenac sodium and 200 µg misoprostol are defined, using the mini-tablets described in example 8.

The region 1 is made of 8 extended release film coated mini-tablets and the region 2 of one immediate release mini-tablets.

The total net weight of the HPMC capsule is 373 mg.

Example 10

HPMC Capsules containing film coated pellets and a powder

HPMC based, 0 size capsules dosed at 75 mg of diclofenac sodium and 200 µg misoprostol are defined.

The region 1 contains film coated extended release pellets. Uncoated pellets are made via an aqueous granulation process, coated with a suitable retardant aqueous formulation and overcoated with a protective coat.

The region 2 is made of an immediate release powder.

Preparation of the 2 regions occurs separately and they are introduced in the empty 0 size HPMC capsules using a suitable capsule filling machine.

The total net weight of the HPMC capsule is 420 mg.

| Diclofenac sodium uncoated pellets (130 mg) | |
|---|---|
| Diclofenac sodium | 75.0 mg |
| Microcristalline cellulose | 15.0 mg |
| Lactose | 26.0 mg |

-continued

| Diclofenac sodium uncoated pellets (130 mg) | |
|---|---|
| Povidone K30 | 7.5 mg |
| Sucrose stearate | 6.5 mg |
| Purified water* | |

*Removed during the process

| Extended release coating of pellets (7.6 mg) | |
|---|---|
| Methacrylate esters copolymer | 4.7 mg |
| Talc | 2.4 mg |
| Hypromellose 5 mPa · s | 0.5 mg |
| Simeticone emulsion | |
| Purified water* | |

*Removed during the process

| Protective coating of ER pellets (3.7 mg) | |
|---|---|
| Hypromellose 5 mPa · s | 3.4 mg |
| Macrogol 6000 | 0.3 mg |
| Purified water* | |

*Removed during the process

| Misoprostol IR powder mixture (278.7 mg) | |
|---|---|
| Misoprostol: HPMC 1% dispersion | 20.0 mg |
| Microcristalline cellulose | 100.0 mg |
| Lactose | 141.0 mg |
| Crospovidone | 15.0 mg |
| Colloidal silicon dioxide | 0.2 mg |
| Hydrogenated castor oil | 2.5 mg |

Example 11

HPMC Capsules Containing Film Coated Pellets and a Mini-tablet

HPMC based, 0 size elongated capsules dosed at 200 mg ketoprofen and 200 µg misoprostol are defined.

The region 1 contains film coated extended release pellets and the region 2 is made of a mini-tablet as in example 8.

The total net weight of the HPMC capsule is 395 mg.

| Ketoprofen ER film coated pellets (350 mg) | |
|---|---|
| Ketoprofen | 200.0 mg |
| Amylum | 50.0 mg |
| Saccharosum | 59.0 mg |
| Shellac gum | 18.5 mg |
| Ethylcellulosum | 18.5 mg |
| Talc | 3.0 mg |
| Colloidal silicon dioxide | 1.0 mg |

Example 12

HPMC Capsules Containing Film Coated Pellets and a Powder

HPMC based, 00 size capsules dosed at 412.5 mg of naproxen sodium and 200 µg of misoprostol are defined.

The region 1 contains the NSAID, partly as immediate release pellets, partly as extended release pellets. The naproxen sodium pellets are coated to avoid direct contact with the second region. The region 2 is made of a free flowing immediate release.

The total net weight of the HPMC capsule is 660 mg.

| Naproxen sodium IR and ER region (560 mg) | |
|---|---|
| Naproxen sodique | 412.5 mg |
| Microcristalline cellulose | 55.0 mg |
| Povidone | 30.0 mg |
| Citric acid | 6.0 mg |
| Magnesium stearate | 12.0 mg |
| Talc | 6.5 mg |
| PEG 6000 | 7.2 mg |
| Ammonium methacrylic ester copolymer type A | 10.0 mg |
| Ammonium methacrylic ester copolymer type B | 10.0 mg |
| Hypromellose 5 mPas | 10.8 mg |

| Stabilized Misoprostol IR region (100 mg) | |
|---|---|
| Misoprostol 1% dispersion HPMC | 20.0 mg |
| Microcristalline cellulose | 25.0 mg |
| Lactose | 48.8 mg |
| Crospovidone | 5.0 mg |
| Colloidal silicon dioxide | 0.2 mg |
| Glycerol behenate | 1.0 mg |

Example 13

HPMC Capsules Containing Film Coated Pellets and a Powder

HPMC based, 0 size capsules dosed at 100 mg of diclofenac sodium and 200 µg of misoprostol are defined.

The region 1 contains film coated extended release pellets. Uncoated pellets are made via a aqueous granulation process, coated with a suitable retardant aqueous formulation and overcoated with a protective coat.

The region 2 is made of a free flowing immediate release powder.

Preparation of the 2 regions occurs separately and they are introduced in the empty 0 size HPMC capsules (total net weight: 420 mg) using a suitable capsule filling machine.

| Diclofenac sodium uncoated pellets (180.0 mg) | |
|---|---|
| Diclofenac sodium | 100.0 mg |
| Microcristalline cellulose | 20.0 mg |
| Lactose | 41.2 mg |
| Povidone K30 | 10.0 mg |
| Sucrose stearate | 8.8 mg |
| Purified water* | |

*Removed during the process

| Extended release coating of pellets (10.1 mg) | |
| --- | --- |
| Methacrylate esters copolymer | 6.3 mg |
| Talc | 3.1 mg |
| Hypromellose 5 mPa · s | 0.7 mg |
| Simeticone emulsion | |
| Purified water* | |

*Removed during the process

| Protective coating of ER pellets (4.9 mg) | |
| --- | --- |
| Hypromellose 5 mPa · s | 4.5 mg |
| Macrogol 6000 | 0.4 mg |
| Purified water* | |

*Removed during the process

| Misoprostol IR powder mixture (225 mg) | |
| --- | --- |
| Misoprostol: HPMC 1% dispersion | 20.0 mg |
| Microcrystalline cellulose | 82.0 mg |
| Lactose | 108.8 mg |
| Crospovidone | 12.0 mg |
| Colloidal silicon dioxide | 0.2 mg |
| Hydrogenated castor oil | 2.0 mg |

Example 14

Multiple-unit Tablets

Tablets dosed at 75 mg of diclofenac sodium and 200 μg misoprostol are defined (10 mm diameter biconvex, total weight: 450 mg).

The region 1 contains film coated extended release pellets. Uncoated pellets are made via a aqueous granulation process, coated with a suitable retardant aqueous formulation and overcoated with a protective coat.

The region 2 is made of a free flowing a immediate release powder.

Preparation of the 2 regions occurs separately and after mixture they are compressed using a suitable tabletting machine.

| Diclofenac sodium uncoated pellets (130 mg) | |
| --- | --- |
| Diclofenac sodium | 75.0 mg |
| Microcrystalline cellulose | 15.0 mg |
| Lactose | 26.0 mg |
| Povidone K30 | 7.5 mg |
| Sucrose stearate | 6.5 mg |
| Purified water* | |

*Removed during the process

| Extended release coating of pellets (7.6 mg) | |
| --- | --- |
| Methacrylate esters copolymer | 4.7 mg |
| Talc | 2.4 mg |
| Hypromellose 5 mPa · s | 0.5 mg |

-continued

| Extended release coating of pellets (7.6 mg) | |
| --- | --- |
| Simeticone emulsion | |
| Purified water* | |

*Removed during the process

| Protective coating of ER pellets (3.7 mg) | |
| --- | --- |
| Hypromellose 5 mPa · s | 3.4 mg |
| Macrogol 6000 | 0.3 mg |
| Purified water* | |

*Removed during the process

| Misoprostol IR powder mixture (308.7 mg) | |
| --- | --- |
| Misoprostol:HPMC 1% dispersion | 20.0 mg |
| Microcrystalline cellulose | 120.0 mg |
| Lactose | 150.4 mg |
| Crospovidone | 15.0 mg |
| Colloidal silicon dioxide | 0.3 mg |
| Hydrogenated castor oil | 3.0 mg |

Example 15

Multiple-unit Tablets

Tablets dosed at 100 mg of diclofenac sodium and 200 μg misoprostol are defined (10 mm diameter biconvex, total weight: 450 mg).

The region 1 contains film coated extended release pellets. Uncoated pellets are made via a aqueous granulation process, coated with a suitable retardant aqueous formulation and overcoated with a protective coat.

The region 2 is made of an immediate release compressed powder.

Preparation of the 2 regions occurs separately and after mixture they are compressed using a suitable tabletting machine.

| Diclofenac sodium uncoated pellets (173.4 mg) | |
| --- | --- |
| Diclofenac sodium | 100.0 mg |
| Microcrystalline cellulose | 20.0 mg |
| Lactose | 35.0 mg |
| Povidone K30 | 10.0 mg |
| Sucrose stearate | 8.4 mg |
| Purified water* | |

*Removed during the process

| Extended release coating of pellets (10.2 mg) | |
| --- | --- |
| Methacrylate esters copolymer | 6.3 mg |
| Talc | 3.2 mg |

| -continued |  |
|---|---|
| Extended release coating of pellets (10.2 mg) | |
| Hypromellose 5 mPa.s | 0.7 mg |
| Simeticone emulsion | |
| Purified water* | |

*Removed during the process

| Protective coating of ER pellets (4.9 mg) | |
|---|---|
| Hypromellose 5 mPa · s | 4.5 mg |
| Macrogol 6000 | 0.4 mg |
| Purified water* | |

*Removed during the process

| Misoprostol IR powder mixture (261.5 mg) | |
|---|---|
| Misoprostol:HPMC 1% dispersion | 20.0 mg |
| Microcristalline cellulose | 105.0 mg |
| Lactose | 120.7 mg |
| Crospovidone | 13.0 mg |
| Colloidal silicon dioxide | 0.3 mg |
| Hydrogenated castor oil | 2.5 mg |

Examples of Ingredients Used for the Development of the Different Formulations

| Ingredients | Suppliers | Function | Comments |
|---|---|---|---|
| Diclofenac sodium | Amoli Organics (Mumbai, India) Cambrex Profarmaco (Landen, Belgium) | Active ingredient | Extended release |
| Misoprostol:HPMC (1:100) | Cascade Biochem (Cork, Ireland) | Active ingredient | Stabilized Dispersion, IR. |
| Methocel K4M, K100 and E5 (Hypromellose) | Colorcon (West Point, USA) | Hydrophilic polymer | Retardant, stabilizing and film coating agent |
| Ethocel 10 mPa · s (Ethylcellulose) | Dow (Midland, USA) | Inert polymer | Retardant |
| Kollidon K25 | BASF (Ludwigshafen, Germany) | Binder | Wet granulation |
| Pharmatose 200 mesh and DCL11 | DMV (Veghel, Netherlands) | Diluent | Wet granulation, dry compression |
| Emcompress (dibasic calcium phosphate | Penwest Pharmaceuticals Co (Patterson, USA) | Diluent | |
| Avicel PH101 et 102 Microcristalline cellulose | FMC (Philadelphia, USA) | Binder | Dry compression, pelletisation |
| NaH₂PO₄.1H₂O | Merck (Belgium) | Buffering agent | pH regulator |
| Citric acid monohydrate | Fédéra (Brussel, Belgium) | Acidifying agent | pH regulator |
| Compritol 888ATO | Gattefossé (Saint Priest, France) | Lubricant | Glycerol behenate |
| Magnesium stearate | UCB (Brussel, Belgium) | Lubricant | |
| Aerosil 200 | Degussa AG (Frankfurt, Germany) | Glidant | |
| Polyplasdone XL | ISP (NJ, USA) | Disintegrant | |
| Cutina HR | | | Hydrogenated castor oil |
| Natrosol 250HMX (Hydroxyethyl Cellulose) | Hercules Ltd (Aqualon) Salford, UK | Hydrophilic polymer | Retardant |
| Eudragit NE30D (Methacrylate esters copolymer) | Röhm GmbH Darmstadt Germany | Barrier coating agent | |
| Macrogol 6000 | Merck München, Germany | Plasticizer | |
| Talc | Aldrich Steinheim, Germany | Anti-adherent agent | |
| Sucrose emulsion | Croda Yorkshire, UK | Lubricant | |
| Simeicon emulsion | Dow Corning Midland Michigan USA | Anti-foaming agent | |
| HPMC Capsules | Shionogi Qualicaps Alcobendas Madrid Spain | Container | Low moisture content |

The invention claimed is:

1. A pharmaceutical composition comprising;
an extended-release first portion made of one or several units containing therapeutically effective amounts of NSAJDs mixed with at least one retardant material for extended release delivery of the non-steroidal anti-inflammatory drugs (NSAJDs) presenting a controlled availability of the non-steroidal anti-inflammatory drug (NSAJDs) alongside the gastrointestinal tract;
an immediate release second portion made of a powder of one or several units containing therapeutically effective amounts of a stabilized misoprostol and a pharmaceutical carrier for the immediate release of said stabilised misoprostol, and wherein the extended release first portion and the immediate release second portion are encapsulated within a capsule made of hydroxyl-propyl-methyl-cellulose (HPMC) polymer.

2. The pharmaceutical composition according to claim 1, wherein the first and second portions are separated by a third portion.

3. The pharmaceutical composition according claim 1, wherein the non-steroidal anti-inflammatory drug (NSAID) is selected from the group consisting of aceclofenac, diclofenac, diflunisal, fenbufen, flufenamic acid, ibuprofen, indomethacin, ketoprofen, meclofenamate sodium, meloxicam, mefenamic acid, nabumetone, naproxen, piroxicam, suprofen, tiaprofenic acid, acetylsalicylic acid, flurbiprofen, ketorolac, oxaprozin, sulindac, tenoxicam, tiaprofenic acid and suitable salts thereof.

4. The pharmaceutical composition according to claim 1, wherein the retardant material of the first portion is selected from the group consisting of lipidic materials, acrylic and methacrylic acid polymers and copolymers, alkyl celluloses, gums, protein derived materials and a mixture thereof.

5. The pharmaceutical composition according to claim 1, wherein the non-steroidal anti-inflammatory drug (NSAID) is diclofenac, ketoprofen, ibuprofen, meloxicam or naproxen.

6. The pharmaceutical composition according to the claim 5 wherein the stabilized misoprostol is stabilized by a dispersion of the misoprostol in hydroxy-propylmethylcellulose (HPMC) or polyvinylpyrrolidone (PVP).

7. A method for the treatment of inflammatory conditions or diseases in a mammal patient, including the human, that comprises the step of administrating a sufficient amount of the pharmaceutical composition according to claim 1, to said mammal patient.

8. The method according to claim 7, wherein said inflammatory condition or disease is osteoarthritis or rheumatoid arthritis.

9. The method of claim 7, wherein the pharmaceutical composition is administered as a dual release formulation allowing a one a day or twice a day dosing into humans.

10. The pharmaceutical composition of the claim 4, wherein the retardant material of the first portion is a lipidic material selected from the group consisting of waxes, glycerides or aliphatic alcohols.

11. The pharmaceutical composition of claim 4, wherein the retardant material of the first portion is an acrylic or methacylic acid polymer selected from the group consisting of methylacrylate polymers, methyl methylacrylate copolymers, ethoxyethyl methacrylate polymers, cyanoethylmethacrylate polymers, aminoalkyl methacrylate copolymers, poly (acetylic acid), poly (methacrylic acid), methacrylic acid alkylamine copolymers, poly(methyl methacrylate) polymers, poly (methacrylic acid)(anhydride), polymethacrylate polymers, polyacrylamide, poly (methacrylic acid anhydride), glycidyl methacryalte copolymers or a mixture thereof.

12. The pharmaceutical composition of claim 4, where the retardant material of the first portion is alkyl celluloses-selected from the group consisting of hydroxypropylmethylcelluloses (HPMC), hydroxymethylcelluloses (HEC), methylcelluloses (MC), ethylcelluloses (EC), sodium carboxymethylcelluloses (NaCMC) and a mixture thereof.

13. The pharmaceutical composition of the claim 6, wherein the retardant material of the first portion is lipidic material selected from the group consisting of waxes, glycerides or aliphatic alcohols or a mixture thereof.

14. The pharmaceutical composition of claim 6, wherein the retardant material of the first portion is acrylic or methacylic acid polymer selected from the group consisting of methylacrylate polymers, methyl methylacrylate copolymers, ethoxyethyl methacrylate polymers, cyanoethylmethacrylate polymers, aminoalkyl methacrylate copolymers, poly (acetylic acid), poly (methacrylic acid), methacrylic acid alkylamine copolymers, poly(methyl methacrylate) polymers, poly (methacrylic acid)(anhydride), polymethacrylate polymers, polyacrylamide, poly (methacrylic acid anhydride), glycidyl methacryalte copolymers or a mixture thereof.

15. The pharmaceutical composition of claim 6, where the retardant material of the first portion is alkyl celluloses selected from the group consisting of hydroxypropylmethylcelluloses (HPMC), hydroxymethylcelluloses (HEC), methylcelluloses (MC), ethylcelluloses (EC), sodium carboxymethylcelluloses (NaCMC) and a mixture thereof.

16. A method for the treatment of inflammatory conditions or diseases in a mammal patient, including the human, that comprises the step of administrating a sufficient amount of the pharmaceutical composition according to claim 6, to said mammal patient.

17. The method according to claim 16, wherein said inflammatory condition or disease is osteoarthritis or rheumatoid arthritis.

18. The method of claim 16, wherein the pharmaceutical composition is administrated as a dual release formulation allowing a one a day or twice a day dosing into humans.

* * * * *